(12) United States Patent
Herskowitz et al.

(10) Patent No.: US 6,414,209 B1
(45) Date of Patent: Jul. 2, 2002

(54) CATALYST FOR CONVERTING PARAFFINIC HYDROCARBON INTO CORRESPONDING OLEFIN

(75) Inventors: Mordechay Herskowitz, Maltar; Shimson Kogan, Beer-Sheva, both of (IL)

(73) Assignees: Mannesman AG, Dusseldorf (DE); K.T.I. Group B.V., Zoetermeer (NL)

( * ) Notice: Subject to any disclaimer, the term of this patent is extended or adjusted under 35 U.S.C. 154(b) by 0 days.

(21) Appl. No.: 09/581,414

(22) PCT Filed: Nov. 23, 1998

(86) PCT No.: PCT/DE98/03495

§ 371 (c)(1),
(2), (4) Date: Sep. 25, 2000

(87) PCT Pub. No.: WO99/29420

PCT Pub. Date: Jun. 17, 1999

(30) Foreign Application Priority Data

Dec. 10, 1997 (DE) .......................................... 197 56 292

(51) Int. Cl.[7] ...................... B01J 27/185; B01J 27/138; B01J 23/00; C07C 5/333

(52) U.S. Cl. ...................... 585/661; 585/654; 585/660; 502/213; 502/226; 502/230; 502/231; 502/303; 502/310; 502/314

(58) Field of Search ................................. 585/654, 660, 585/661; 502/208, 210, 213, 215, 224, 226, 230, 303, 304, 306, 310, 314

(56) References Cited

U.S. PATENT DOCUMENTS

| | | | |
|---|---|---|---|
| 4,551,574 A | 11/1985 | Imai et al. | ................... 585/660 |
| 4,677,237 A | 6/1987 | Imai et al. | ................... 585/444 |

FOREIGN PATENT DOCUMENTS

| | | |
|---|---|---|
| EP | 0 749 779 | 12/1996 |
| WO | WO 94 29021 | 12/1994 |

*Primary Examiner*—Walter D. Griffin
*Assistant Examiner*—Tam M. Nguyen
(74) *Attorney, Agent, or Firm*—Frishauf, Holtz, Goodman, Langer & Chick, P.C.

(57) ABSTRACT

The invention relates to a calcinated catalyst for converting paraffinic hydrocarbon into corresponding olefin through dehydrogenation. The catalyst is an oxidic, heat-stable carrier material and contains a catalytic active constituent, which is applied on the carrier material and has the following composition (in wt. % in relation to the entire weight of the catalyst): a) 0.2 to 2.0% of at least one element of the groups Pt and Ir and, acting as a promoter, a combination of elements from the six following groups of substances: b) 0.2 to 5.0% of at least one of the following elements Ge, Sn, Pb, Ga, In, Tl; c) 0.1 to 5.0% of at least one of the following elements Li, Na, K, Rb, Cs, Fr; d) 0.2 to 5.0% of at least one of the following elements Fe, Co, Ni, Pd; e) 1.0 to 5.0% P; f) 0.2 to 5.0% of at least one of the following elements Be, Mg, Ca, Sr, Ba, Ra and lanthanides and g) 0.1 to 2.0% Cl.

25 Claims, 4 Drawing Sheets

Fig. 1

| Catalyst | Composition (weight %) | | | | | | | Conversion (%) | Selectivity (mol-%) | Propylene Yield (mol-%) |
|---|---|---|---|---|---|---|---|---|---|---|
| | a | b | c | d | e | f | g | | | |
| A | 0.6 Pt | 2 Sn | 1 K | 1 Ni | 1 P | 3 Ca | 0.5 Cl | 38 | 88 | 33.4 |
| B | 0.6 Pt | 2 Sn | 1 K | 1 Ni | 2 P | 3 Ca | 0.5 Cl | 44.7 | 94 | 42 |
| C | 0.6 Pt | 2 Sn | 1 K | 1 Ni | 2.5 P | 3 Ca | 0.5 Cl | 49 | 94 | 46 |
| D | 0.6 Pt | 2 Sn | 1 K | 1 Ni | 3.5 P | 3 Ca | 0.5 Cl | 55.5 | 91 | 50.5 |
| E | 0.6 Pt | 2 Sn | 1 K | 1 Ni | 5 P | 3 Ca | 0.5 Cl | 40.0 | 95 | 38 |
| F*) | 0.6 Pt | 2 Sn | 1 K | 1 Ni | - | - | 0.5 Cl | 41.2 | 68 | 28 |
| G*) | 0.6 Pt | 2 Sn | 1 K | - | 2 P | 3 Ca | 0.5 Cl | 15.4 | 91 | 1.4 |
| H | 0.6 Pt | 2 Sn | 1.5 K | 3.5 Fe | 3 P | 3 Ca | 0.5 Cl | 52 | 93 | 48.4 |
| K | 0.6 Pt | 2 Sn | 1.5 K | 1 Pd | 3 P | 3 Ca | < 2 Cl | 48 | 95.5 | 45.8 |
| L | 0.6 Pt | 2 Sn | 1 K | 1 Ni | 3 P | 3 Ce | 0.5 Cl | 55 | 89.5 | 49.2 |
| M | 0.6 Pt | 2 Sn | 2.2 K | 1 Ni | 2 P | 3 Ca | 0.5 Cl | 47.5 | 92.5 | 43.9 |
| N | 0.6 Pt | 2 Sn | 2 Cs | 1 Ni | 3 P | 3 Ca | 0.5 Cl | 57 | 90.5 | 51.6 |
| R | 0.6 Pt | 2 Sn | 1 K | 1 Ni | 2 P | 2 Ba | 0.5 Cl | 52 | 93 | 48.4 |
| S*) | 0.6 Pt | 2 Sn | 1 K | - | - | - | 0.5 Cl | 34 | 88 | 30 |

*) Comparison examples

Fig. 2

Long Term Test
P = 1 bar
$H_2O/C_3$ = 4.5 (mol)
WHSV = 1.2 h$^{-1}$

| | Duration of Operation (in hours) | | | | | | | | | | | | | | | |
|---|---|---|---|---|---|---|---|---|---|---|---|---|---|---|---|---|
| | 5 | 10 | 15 | 20 | 30 | 40 | 50 | 60 | 70 | 80 | 90 | 100 | | | | |
| Catalyst B | | | | | | | | | | | | | | | | |
| Temperature (°C) | 550 | 550 | 580 | 580 | 580 | 580 | 580 | 580 | 580 | 580 | 580 | 590 | | | | |
| Conversion (%) | 51 | 54 | 64 | 64.5 | 63.5 | 62 | 60 | 58 | 58 | 57 | 54 | 57.5 | | | | |
| Selectivity (mol-%) | 91 | 92 | 87 | 88 | 89 | 90 | 90 | 92 | 92 | 92 | 93 | 91 | | | | |
| Catalyst L | | | | | | | | | | | | | | | | |
| Temperature (°C) | 550 | 550 | 550 | 550 | 550 | 550 | 550 | 550 | 550 | 550 | 550 | 550 | | | | |
| Conversion (%) | 56 | 56 | 56 | 56 | 55 | 55 | 55 | 55 | 55 | 54 | 54 | 54 | | | | |
| Selectivity (mol-%) | 90 | 91 | 91 | 92 | 93 | 93 | 93 | 94 | 94 | 95 | 95 | 95 | | | | |
| Catalyst S | | | | | | | | | | | | | | | | |
| Temperature (°C) | 550 | 560 | 570 | 580 | | | | | | | | | | | | |
| Conversion (%) | 34 | 36 | 38 | 40 | | | | | | | | | | | | |
| Selectivity (mol-%) | 89 | 87 | 86 | 85 | | | | | | | | | | | | |

| Long Term Test P = 2 bar WHSV = 1.2 h⁻¹ | | Duration of Operation (in hours) | | | | | | | | | | |
|---|---|---|---|---|---|---|---|---|---|---|---|---|
| | | 5 | 10 | 20 | 30 | 40 | 50 | 60 | 70 | 80 | 90 | 100 |
| Catalyst B $H_2O/C_3 = 6$ (mol) | Temperature (°C) | 580 | 580 | 580 | 580 | 580 | 580 | 580 | 580 | 580 | 590 | 590 |
| | Conversion (%) | 57 | 56 | 56 | 55 | 55 | 54 | 53 | 51 | 50 | 52 | 50 |
| | Selectivity (weight %) | 85 | 86 | 86 | 87 | 88 | 88 | 89 | 89 | 89 | 88 | 88 |
| | Propylene Yield (weight %) | 48.5 | 48 | 48 | 48 | 48.5 | 47.5 | 47 | 45.5 | 44.5 | 46 | 44 |
| Catalyst D $H_2O/C_3 = 4$ (mol) | Temperature (°C) | 580 | 580 | 580 | 580 | 580 | 580 | 580 | 580 | 600 | 600 | 600 |
| | Conversion (%) | 55 | 56 | 56 | 54 | 53 | 53 | 52 | 50 | 57 | 53 | 50 |
| | Selectivity (weight %) | 85 | 86 | 86 | 88 | 90 | 90 | 90 | 91 | 89 | 89 | 90 |
| | Propylene Yield (weight %) | 47 | 48 | 48 | 47.5 | 47.5 | 47.5 | 47 | 45.5 | 50.5 | 47 | 45 |

Fig. 3

Fig. 4

| Temperature (°C) | O₂ Content in Feed Material | Conversion (%) | Selectivity (mol-%) | Isobutylene Yield (mol-%) |
|---|---|---|---|---|
| 530 | None | 59 | 96.5 | 56.9 |
| 540 | None | 61.5 | 96 | 59 |
| 550 | None | 63.5 | 96 | 61 |
| 550 | 0.4 | 66.5 | 96 | 62.8 |
| 550 | 0.7 | 66 | 94 | 62 |
| 550 | 1.4 | 66 | 93 | 61.4 |

CATALYST FOR CONVERTING PARAFFINIC HYDROCARBON INTO CORRESPONDING OLEFIN

FIELD OF THE INVENTION

The invention relates to a calcined catalyst for converting paraffin hydrocarbons into corresponding olefins by dehydrogenation, wherein the catalyst contains an oxidic, thermally stabilized substrate material and a catalytically active component that is applied to the substrate material. The invention also relates to a method for converting paraffin hydrocarbons into corresponding olefins, in which a stream of the paraffin hydrocarbons is mixed with water vapor and put into contact with a catalyst. The paraffins addressed within the scope of the invention are in the range from $C_2$ to $C_{20}$, preferably in the range from $C_2$ to $C_5$.

BACKGROUND OF THE INVENTION

A large number of catalysts that are used to dehydrogenate paraffins are known. Such catalysts have a thermally stabilized, inorganic oxide as the substrate material, an active component (preferably a metal of the platinum group), and one or more promoters. Active $Al_2O_3$, which has an especially large specific surface area, is often used as the substrate material.

U.S. Pat. No. 4,788,371, describes a catalyst and a method for dehydrogenating paraffins in a water vapor atmosphere. The substrate of the catalyst comprises $Al_2O_3$ and is coated both with a noble metal (preferably platinum) and several promoters, which are selected from Group III or IV of the Periodic table and the gallium or germanium subgroup (preferably tin) and alkaline metals (preferably potassium or cesium). The dehydrogenation method described in this reference can function in the presence of a limited amount of oxygen, which is used to heat the reaction zone by combusting hydrogen.

From U.S. Pat. No. 5,220,091, a catalyst and a method for dehydrogenating $C_2$ to $C_8$ paraffins in the presence of water vapor is known. The catalyst used here comprises platinum (approximately 0.7 weight %) as well as zinc aluminate and potassium aluminate. In the dehydrogenation of isobutane ($iC_4$), a conversion rate of 50% and a selectivity of 94 mol-% was attained; the pressure was adjusted to P=3.5 bar, the temperature was adjusted to T=571° C., and the ratio of steam to isobutane (mol) was adjusted to 3.96. After a cycle time of 7 hours, the catalyst had to be subjected to a reactivation treatment by oxidative regeneration.

A further method and a catalyst for dehydrogenation of organic compounds is described in European Patent Disclosure EP 0 568 303 A2. This method uses a hydrogen atmosphere. The catalyst contains nickel and various promoters of Groups I-VIII of the Periodic table on a non-acid substrate material (base-treated $Al_2O_3$, zeolites, etc.). The special feature of the technology described in this reference is many dehydrogenation zones with intermediate zones for oxidizing hydrogen produced, on a special catalyst. The best results in the dehydrogenation of isobutane were obtained with a nickel catalyst (3.4% Ni and 3.4% Cr on a Ba-exchanged zeolite L), using a temperature of T=602° C., a molar ratio $H_2/iC_4$=6 and a space velocity of WHSV=650 $h^{-1}$. Over an operating duration of 6 hours, the conversion rate was 30–36.6% and the selectivity was 75.1–83.4%. For an operating duration of 50–65 hours, the conversion rate was in the range from 22.2–27.9% and the selectivity was in the range from 78.8–81.1%.

Another catalyst and a method for dehydrogenation of hydrocarbons is known from International Patent Disclosure WO 94/29021. The method operates in a water vapor and hydrogen atmosphere, using a platinum catalyst, which as promoters contains elements of the tin subgroup and alkaline metals (potassium, cesium). The special feature of the catalyst is a special substrate material, which comprises a mixture of magnesium oxide and aluminum oxide. This composition requires a special pretreatment of the catalyst, which comprises a reduction with hydrogen, a calcination in an $O_2$ atmosphere, and another reduction (called an ROR treatment). With this ROR treatment, the catalyst has an activity three times higher than without this treatment. The dehydrogenation of propane ($C_3$) with the aid of the described catalyst, at a temperature of T=600° C., a pressure of P=1 bar, a space velocity WHSV=1.3 $h^{-1}$ and a ratio of $H_2/H_2O/C_3$=0.14/1.2/1 and an operating time of 25 hours, led to the following results: The propylene yield was 55.5 mol-%, and the selectivity was 96.1 mol-%. A comparative test described in this reference, using a catalyst known from U.S. Pat. No. 4,788,371, under otherwise identical conditions, led to a propylene yield of 25.7 to 29.7 mol-% and a selectivity of 95.0 to 95.9 mol-%. Thus WO 94/29021 represents the performance standard thus far in the field of catalytic conversion of paraffin hydrocarbons into corresponding olefins.

OBJECTS AND SUMMARY OF THE INVENTION

The object of the present invention is to disclose a catalyst for converting paraffin hydrocarbons into corresponding olefins that not only assures high effectiveness, or in other words has a good conversion rate and good selectivity, but furthermore exhibits high operating stability; that is, it can be used over comparatively long cycle times before having to be subjected to a reactivation treatment. The production of the catalyst should be as simple as possible. A method for converting paraffin hydrocarbons into corresponding olefins, which leads to good olefin yields and can be operated over cycle times that are as long as possible before catalyst reactivation has to be done is also to be disclosed.

In terms of the catalyst, this object is attained by the characteristics recited in claim 1, and in terms of the method, it is attained by the characteristics recited in claim 16. Advantageous features of the invention are defined by the dependent claims.

DETAILED DESCRIPTION OF PREFERRED EMBODIMENTS OF THE INVENTION

In the course of the tests that led to the present invention, it was discovered that catalysts known per se on $Al_2O_3$ substrates, which have platinum, a metal of the germanium or gallium group (preferably tin or indium) and an alkali metal (preferably potassium or cesium) can be improved substantially in terms of their activity by the addition of certain promoters. Along with progress in increasing the catalytic activity, it can be noted as a particular advantage of the invention that no special activation treatment, such as the ROR treatment, is necessary in the production of the catalyst. Furthermore, in the use of the catalyst, there is no need to add hydrogen to the feed material. On the contrary, the catalyst functions quite reliably in the presence of oxygen. The production of the catalyst can be done by known methods on conventional substrate materials.

The calcined catalyst of the invention comprises a thermally stabilized substrate material, onto which a catalytically active component is applied. The substrate material is preferably aluminum oxide, in particular in the form of Θ-Al$_2$O$_3$. The catalytically active component comprises the material groups a) through g), explained in further detail hereinafter, in which the quantities are given in weight % and are referred to the total weight of the The material group a) includes the elements Pt and Ir, which represents the substance that is catalytically effective in the narrower sense, while the other material groups can be considered essentially as promoters, which promote the catalytic activity. The catalyst must have at least one of the elements of group a), specifically in a quantity of from 0.2 to 2%. The element Pt is especially preferred. It is recommended that the content of the element or elements of material group a) be limited to 0.3 to 0.6%.

As the promoter in the catalyst of the invention, at least one of each of the elements listed in material groups b) through g) described below must be represented. The material group b) comprises the elements Ge, Sn, Pb, Ga, In and Tl. The content of material group b) in the catalyst is in the range from 0.2 to 5%, and expediently in the range from 0.5 to 2.5%. The use of Sn is especially preferred.

The material group c) includes the elements Li, Na, K, Rb, Cs and Fr and has a quantitative proportion of from 0.1 to 5%, and preferably 0.5 to 1.5%. The elements K and Cs from this material group have proved to be especially effective.

The material group d) includes the elements Fe, Co, Ni and Pd. Its content is in the range from 0.2 to 5%, and preferably in the range from 1.0 to 3%. The use of Fe and/or Ni from this material group is especially expedient.

As a further promoter, the catalyst of the invention has a proportion (e) of P on an order of magnitude of from 1.0 to 5%. It is recommended that the P content be limited to from 2.0 to 4.0%. The material group f), whose quantity is limited to a proportion of from 0.2 to 5% and preferably to a range from 1.0 to 3%, includes the elements Be, Mg, Ca, Sr, Ba, Ra, and the group comprising the lanthanides. From this group, the elements Ca and Ba are preferred.

Finally, the catalyst has a proportion (g) of Cl on an order of magnitude of from 0.1 to 2%. The element Cl is a component that does not act as a promoter in the strict sense of the word, but that improves the initial dispersion of the noble metal in the catalyst. On the other hand, Cl promotes undesired secondary reactions at the onset of use of the catalyst. The initial content should therefore be clearly limited.

With the present invention, a method for converting paraffin hydrocarbons into corresponding olefins is also proposed in which a stream of the paraffin hydrocarbons is mixed with water vapor and put into contact with a catalyst that has the above-described composition at a temperature in the range from 500 to 650° C. and at a pressure of at least 1.0 bar (absolute). Expediently, the addition of H$_2$ to the stream of paraffin hydrocarbons and water vapor that until now was often usual is expediently dispensed with. It is recommended that the molar ratio of the water vapor to the paraffin hydrocarbons be adjusted within a range from 0.5:1 to a maximum of 10:1, and preferably within a range from 1:1 to 6:1. It has proved to be especially advantageous to use the catalyst of the invention with feed materials that contain hydrocarbons of the group comprising the C$_2$ to C$_6$ paraffins. To improve the conversion, it is advantageous to add O$_2$ to the stream of paraffin hydrocarbons, because the oxygen reacts with the liberated hydrogen and thus shifts the equilibrium of the reaction. A molar ratio of the paraffin hydrocarbons to the O$_2$ in the range from 1:0.2 to 1:1.5, and in particular in the range from 1:0.3 to 1:0.7 has proved especially expedient.

The invention will be described in further detail below in terms of exemplary embodiments.

EXAMPLE 1

To produce a catalyst, 14 g of Θ-Al$_2$O$_3$ as the substrate material (specific surface area, 130 m$^2$/g) were impregnated with an aqueous solution of two salts. This solution was formed from 15 cm$^3$ of water into which 2.5 g of potassium nitrate (tetrahydrate) and 0.7 g of nickel nitrate (hexahydrate) were added. The impregnated substrate material remained at room temperature for 10 hours and was then dried for a duration of 5 hours at 100° C. and for a duration of a further 5 hours at 150° C. The dry material was then calcined for 2 hours at 350° C. and for a further 2 hours at 550° C., the rate of the temperature increase being approximately 1° C./min.

The material produced in this way was then impregnated with orthophosphoric acid (55 g of 84% phosphoric acid in 18 cm$^3$ of water). After that, the material was dried and re-calcined in the manner described above. Next, the material was impregnated with tin dichloride (0.29 g of SnCl$_2$× 2H$_2$O in 20 cm$^3$ of ethanol with the addition of 0.2 g of concentrated hydrochloric acid, stirred constantly with slight heating to up to 40° C.), dried, and again calcined as described above.

After that, this material was impregnated with 18 cm$^3$ of an aqueous solution of hexachloroplatinic acid (0.093 g of metallic Pt), dried, and calcined again in the same manner. Finally, the material was impregnated with 18 cm$^3$ of an aqueous solution that contained 0.36 g of KNO$_3$, then dried, and again calcined as described. In this way, a catalyst was produced which had the following composition, in weight % referred to the total weight of the catalyst:

| | |
|---|---|
| 3% | Ca |
| 1% | Ni |
| 1% | P |
| 2% | Sn |
| 1% | K |
| 0.6% | Pt |
| 0.5% | Cl |

This catalyst is listed as catalyst A in Table 1.

EXAMPLE 2

The effectiveness of catalyst A was tested in an experiment lasted 5 hours, in which propane was dehydrogenated in a steam atmosphere. The followed values were established as the test conditions:

| | |
|---|---|
| P = | 1 bar |
| T = | 550° C. |
| WHSV = | 1.2 h$^{-1}$ |
| H$_2$O/C$_3$ = | 4.5 (mol) |

The resultant conversion rate, selectivity, and propane yield are shown in Table 1.

EXAMPLE 3

In a way corresponding to what is described in Example 1, catalysts B, C, D and E were produced; only the P content was increased in stages to 2.0% (B), 2.5% (C), 3.5% (D), and 5.0% (E). The composition of catalysts B through E is shown in Table 1. This table also shows the results obtained in an effectiveness test of these catalysts; the test conditions were the same as in Example 2.

EXAMPLE 4

For comparison with the catalysts A through E of the invention, a catalyst F was also produced analogously to the manner described in Example 1, but neither P nor Ca was included in the composition. This catalyst was also tested under the conditions listed in Example 2. The results are shown in Table 1.

EXAMPLE 5

As the second comparison example, a catalyst G was produced analogously to the manner described in Example 1; it had the same composition as catalyst B, except that it did contain any Ni. This catalyst G was also tested under the test conditions of Example 2. The results are shown in Table 1.

EXAMPLE 6

A catalyst H was produced analogously to the manner described; its composition differed from catalyst D in that the K content was raised to 1.5% and the P content was raised to 3%, and furthermore, instead of 1% Ni, 3.5% Fe was added. The Fe addition was made in the form of an aqueous solution of $Fe(NO_3)_3 \times 9H_2O$. This catalyst was again tested under the conditions of Example 2.

The results are shown in Table 1.

EXAMPLE 7

A catalyst K was produced analogously to the manner described; in its composition, it differed substantially from catalyst H only in that instead of 3.5% Fe, 1% Pd was added. The palladium was added in the form of an aqueous solution of $PdCl_2$, which contained 3% HCl. The effectiveness was again tested under the conditions of Example 2. The results are shown in Table 1.

EXAMPLE 8

A catalyst L was produced analogously to the manner described; it differed from catalyst D only in that the P content was reduced from 3.5% to 3.0%, and instead of 3% Ca, 3% Ce was added. This catalyst was also tested under the conditions of Example 2. The results are shown in Table 1.

EXAMPLE 9

A catalyst M was produced in the same way as catalyst B, with the only difference that the K content was increased from 1% to 2.2%. This catalyst was also tested under the conditions of Example 2. The results are shown in Table 1.

EXAMPLE 10

A catalyst N was produced in the same way as catalyst D, except that the P content was reduced from 3.5% to 3%, and instead of 1% K, 2% Cs was added here. The catalyst was again tested under the conditions of Example 2. The results are shown in Table 1.

EXAMPLE 11

A catalyst R was produced in the same way as catalyst B; the composition differed from the composition of catalyst B only in that instead of 3% Ca, 2% Ba was added here. The barium was added in the form of a nitrate in aqueous solution. The catalyst was again tested under the conditions of Example 2. The results are shown in Table 1.

EXAMPLE 12

Again for comparison with catalysts of the invention, a catalyst S was made in the manner described in Example 1, but the elements Ni, Ca and P were left out of the composition. The catalyst was again tested under the conditions of Example 2. The results are shown in Table 1.

It is quite clear from Table 1 that the addition of Ca, Ni and P to platinum-tin-potassium catalysts known per se causes a quite considerable increase in catalyst activity with regard to the dehydrogenation of paraffins in a steam environment. This is shown by the catalysts A through E of the invention, for example, in comparison to the comparison catalyst S. For one skilled in the art, this is a completely unexpected effect, because the addition of only one of these components (namely Ni) or only two of these components (namely Ca and P) has a negative influence on the catalyst effectiveness, as the two catalysts F and G, which are not according to the invention, show in comparison to catalyst S, also not of the invention. Furthermore, it should be noted that it is widely known that P is a catalyst poison in catalytic dehydrogenation by means of a noble metal catalyst. Table 1, for catalysts H and K, shows that the promoter effect is assured even if instead of Ni, a different metal in the iron group (Group VIII), which is considered a catalyst poison with respect to platinum, or palladium is used. It can be seen from the example of catalysts L and R that instead of calcium, a different alkaline earth metal (such as barium) or a rare earth metal (such as cerium) can also be employed.

EXAMPLE 13

To test the long-term effectiveness, catalysts B, L and S were subjected to an operation test, in which the same conditions were established as in Example 2. The only difference was that the test duration was prolonged substantially. The results are shown in Table 2. For the comparison catalyst S, the test had to be stopped after only about 20 hours of operation, because of carbonization.

EXAMPLE 14

Catalysts B and D were also subjected to a long-term test in the dehydrogenation of propane. In contrast to the test conditions of Example 13, however, the following parameter values were established:

| | |
|---|---|
| P = | 2 bar |
| T = | 580° C. |
| WHSV = | 1.2 h$^{-1}$ |
| H$_2$O/C$_3$ = | 6 (mol) |

For catalyst B, the $H_2O/C_3$ ratio was adjusted to 4 (mol), instead of 6 (mol). The results of the two tests are shown in Table 3.

EXAMPLE 15

Catalyst B was tested in an experiment in which over a test duration of 5 hours, isobutane was dehydrogenated under the following conditions:

| | |
|---|---|
| P = | 1 bar |
| T = | 530–550° C. |
| WHSV = | 1.2 h$^{-1}$ |
| H$_2$O/iC$_4$ = | 4 (mol) |

The results are shown in Table 4.

The advantages of the catalysts of the invention are clearly confirmed by the results of the long-term tests shown in Tables 2 and 3. The improved activity and selectivity is exhibited even in the dehydrogenation of other paraffins, such as isobutane. The test results shown for this in Table 4 confirm that the catalyst effectiveness in the dehydrogenation of olefins is assured both in a pure water vapor environment and when oxygen is added (lower half of the measurement results in Table 4). In comparison to the known catalysts described at the outset, the catalyst of the invention also has markedly better activity over a longer operating duration, so that the cycle time between two reactivation treatments is substantially longer.

TABLE 1

| Catalyst | Composition (weight %) | | | | | | | Conversion (%) | Selectivity (mol-%) | Propylene Yield (mol-%) |
|---|---|---|---|---|---|---|---|---|---|---|
| | a | b | c | d | e | f | g | | | |
| A | 0.6 Pt | 2 Sn | 1 K | 1 Ni | 1 P | 3 Ca | 0.5 Cl | 38 | 88 | 33.4 |
| B | 0.6 Pt | 2 Sn | 1 K | 1 Ni | 2 P | 3 Ca | 0.5 Cl | 44.7 | 94 | 42 |
| C | 0.6 Pt | 2 Sn | 1 K | 1 Ni | 2.5 P | 3 Ca | 0.5 Cl | 49 | 94 | 46 |
| D | 0.6 Pt | 2 Sn | 1 K | 1 Ni | 3.5 P | 3 Ca | 0.5 Cl | 55.5 | 91 | 50.5 |
| E | 0.6 Pt | 2 Sn | 1 K | 1 Ni | 5 P | 3 Ca | 0.5 Cl | 40.0 | 95 | 38 |
| F*) | 0.6 Pt | 2 Sn | 1 K | 1 Ni | — | — | 0.5 Cl | 41.2 | 68 | 28 |
| G*) | 0.6 Pt | 2 Sn | 1 K | — | 2 P | 3 Ca | 0.5 Cl | 15.4 | 91 | 14 |
| H | 0.6 Pt | 2 Sn | 1.5 K | 3.5 Fe | 3 P | 3 Ca | 0.5 Cl | 52 | 93 | 48.4 |
| K | 0.6 Pt | 2 Sn | 1.5 K | 1 Pd | 3 P | 3 Ca | <2 Cl | 48 | 95.5 | 45.8 |
| L | 0.6 Pt | 2 Sn | 1 K | 1 Ni | 3 P | 3 Ce | 0.5 Cl | 55 | 89.5 | 49.2 |
| M | 0.6 Pt | 2 Sn | 2.2 K | 1 Ni | 2 P | 3 Ca | 0.5 Cl | 47.5 | 92.5 | 43.9 |
| N | 0.6 Pt | 2 Sn | 2 Cs | 1 Ni | 3 P | 3 Ca | 0.5 Cl | 57 | 90.5 | 51.6 |
| R | 0.6 Pt | 2 Sn | 1 K | 1 Ni | 2 P | 2 Ba | 0.5 Cl | 52 | 93 | 48.4 |
| S*) | 0.6 Pt | 2 Sn | 1 K | — | — | — | 0.5 Cl | 34 | 88 | 30 |

*)Comparison Examples

TABLE 2

Long Term Test
P = 1 bar
H$_2$O/C$_3$ = 4.5 (mol)

| WHSV = 1.2 h$^{-1}$ | Duration of Operation (in hours) | | | | | | | | | | | |
|---|---|---|---|---|---|---|---|---|---|---|---|---|
| | 5 | 10 | 15 | 20 | 30 | 40 | 50 | 60 | 70 | 80 | 90 | 100 |
| Catalyst B | | | | | | | | | | | | |
| Temperature (° C.) | 550 | 550 | 580 | 580 | 580 | 580 | 580 | 580 | 580 | 580 | 580 | 590 |
| Conversion (%) | 51 | 54 | 64 | 64.5 | 63.5 | 62 | 60 | 58 | 58 | 57 | 54 | 57.5 |
| Selectivity (mol-%) | 91 | 92 | 87 | 88 | 89 | 90 | 90 | 92 | 92 | 92 | 93 | 91 |
| Catalyst L | | | | | | | | | | | | |
| Temperature (° C.) | 550 | 550 | 550 | 550 | 550 | 550 | 550 | 550 | 550 | 550 | 550 | 550 |
| Conversion (%) | 56 | 56 | 56 | 56 | 55 | 55 | 55 | 55 | 55 | 54 | 54 | 54 |
| Selectivity (mol-%) | 90 | 91 | 91 | 92 | 93 | 93 | 93 | 94 | 94 | 95 | 95 | 95 |
| Catalyst S | | | | | | | | | | | | |
| Temperature (° C.) | 550 | 560 | 570 | 580 | | | | | | | | |
| Conversion (%) | 34 | 36 | 38 | 40 | | | | | | | | |
| Selectivity (mol-%) | 89 | 87 | 86 | 85 | | | | | | | | |

TABLE 3

Long Term Test
P = 2 bar

| WHSV = 1.2 h$^{-1}$ | | Duration of Operation (in hours) | | | | | | | | | | |
|---|---|---|---|---|---|---|---|---|---|---|---|---|
| | | 5 | 10 | 20 | 30 | 40 | 50 | 60 | 70 | 80 | 90 | 100 |
| Catalyst B H$_2$O/C$_3$ = 6 (mol) | Temperature (° C.) | 580 | 580 | 580 | 580 | 580 | 580 | 580 | 580 | 580 | 590 | 590 |
| | Conversion (%) | 57 | 56 | 56 | 55 | 55 | 54 | 53 | 51 | 50 | 52 | 50 |
| | Selectivity (weight %) | 85 | 86 | 86 | 87 | 88 | 88 | 89 | 89 | 89 | 88 | 88 |
| | Propylene Yield (weight %) | 48.5 | 48 | 48 | 48 | 48.5 | 47.5 | 47 | 45.5 | 44.5 | 46 | 44 |

TABLE 3-continued

| Long Term Test P = 2 bar | | | | | | Duration of Operation (in hours) | | | | | | |
|---|---|---|---|---|---|---|---|---|---|---|---|---|
| WHSV = 1.2 h$^{-1}$ | | 5 | 10 | 20 | 30 | 40 | 50 | 60 | 70 | 80 | 90 | 100 |
| Catalyst D | Temperature (° C.) | 580 | 580 | 580 | 580 | 580 | 580 | 580 | 580 | 600 | 600 | 600 |
| H$_2$O/C$_3$ = 4 (mol) | Conversion (%) | 55 | 56 | 56 | 54 | 53 | 53 | 52 | 50 | 57 | 53 | 50 |
| | Selectivity (weight %) | 85 | 86 | 86 | 88 | 90 | 90 | 90 | 91 | 89 | 89 | 90 |
| | Propylene Yield (weight %) | 47 | 48 | 48 | 47.5 | 47.5 | 47.5 | 47 | 45.5 | 50.5 | 47 | 45 |

TABLE 4

| Temperature (° C.) | O$_2$ Content in Feed Material | Conversion (%) | Selectivity (mol-%) | Isobutylene Yield (mol-%) |
|---|---|---|---|---|
| 530 | None | 59 | 96.5 | 56.9 |
| 540 | None | 61.5 | 96 | 59 |
| 550 | None | 63.5 | 96 | 61 |
| 550 | 0.4 | 66.5 | 96 | 62.8 |
| 550 | 0.7 | 66 | 94 | 62 |
| 550 | 1.4 | 66 | 93 | 61.4 |

We claim:

1. A calcined catalyst for converting paraffin hydrocarbons into corresponding olefins by dehydrogenation, wherein the catalyst contains an oxidic, thermally stabilized substrate material and a catalytically active component that is applied to the substrate material and has the following composition (in weight % of the total weight of the catalyst):
   a) from 0.2 to 2.0% of at least one of the elements of the group comprising Pt and Ir, and as a promoter a combination of elements of each of the following six material groups:
   b) from 0.2 to 5.0% of at least one of the elements Ge, Sn, Pb, Ga, In, and Tl,
   c) from 0.1 to 5.0% of at least one of the elements Li, Na, K, Rb, Cs, and Fr,
   d) from 0.2 to 5.0% of at least one of the elements Fe, Co, Ni, and Pd,
   e) from 1.0 to 5.0% of P,
   f) from 0.2 to 5% of at least one of the elements Be, Mg, Ca, Sr, Ba, Ra and the lanthanides,
   g) from 0.1 to 2% Cl.

2. The catalyst of claim 1, characterized in that the substrate material is Al$_2$O$_3$.

3. The catalyst of claim 1, characterized in that the content of the elements of material group a) is limited to from 0.3 to 0.6%.

4. The catalyst of claim 1, characterized in that the content of the elements of material group b) is limited to from 0.5 to 2.5%.

5. The catalyst of claim 1, characterized in that the content of the elements of material group c) is limited to from 0.5 to 1.5%.

6. The catalyst of claim 1, characterized in that the content of the elements of material group d) is limited to from 1.0 to 3.0%.

7. The catalyst of claim 1, characterized in that the P content is limited to from 2.0 to 4.0%.

8. The catalyst of claim 1, characterized in that the content of the elements of material group f) is limited to from 1.0 to 3.0%.

9. The catalyst of claim 1, characterized in that Pt is selected as the element from group a).

10. The catalyst of claim 1, characterized in that Sn is selected as the element from group b).

11. The catalyst of claim 1, characterized in that K is selected as the element from group c).

12. The catalyst of claim 1, characterized in that Cs is selected as the element from group c).

13. The catalyst of claim 1, characterized in that Fe and/or Ni is selected as the element from group d).

14. The catalyst of claim 1, characterized in that Ca is selected as the element from group f).

15. The catalyst of claim 1, characterized in that Ba is selected as the element from group f).

16. A method for converting paraffin hydrocarbons into corresponding olefins, in which a stream of the paraffin hydrocarbons is mixed with water vapor and put into contact with a catalyst of claim 1 at a temperature in the range from 500 to 650° C. and at a pressure of at least 1.0 bar (absolute).

17. The method of claim 16, characterized in that the stream of paraffin hydrocarbons and the water vapor are free of a H$_2$.

18. The method of claim 16, characterized in that the molar ratio of the water vapor to the paraffin hydrocarbons is at least 0.5:1.

19. The method of claim 16, characterized in that the molar ratio of the water vapor to the paraffin hydrocarbons is limited to a maximum of 10:1.

20. The method of claim 16, characterized in that the molar ratio of the water vapor to the paraffin hydrocarbons is in the range from 1:1 to 6:1.

21. The method of claim 16, characterized in that the hydrocarbons belong the group of C$_2$ to C$_6$ paraffins.

22. The method of claim 16, characterized in that O$_2$ is added to the stream of paraffin hydrocarbons.

23. The method of claim 22, characterized in that the molar ratio of the paraffin hydrocarbons to the O$_2$ is in range from 1:0.2 to 1:0.5.

24. The method of claim 23, characterized in that the molar ratio of the paraffin hydrocarbons to the O$_2$ is in range from 1:0.3 to 1:0.7.

25. The catalyst of claim 2, wherein the substrate material is Θ-Al$_2$O$_3$.

* * * * *